US006462043B1

(12) United States Patent
Maienfisch

(10) Patent No.: US 6,462,043 B1
(45) Date of Patent: Oct. 8, 2002

(54) METHOD FOR PRODUCING SUBSTITUTED-2-NITROGUANIDINE DERIVATIVES

(75) Inventor: Peter Maienfisch, Rodersdorf (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/485,873

(22) PCT Filed: Aug. 14, 1998

(86) PCT No.: PCT/EP98/05166

§ 371 (c)(1),
(2), (4) Date: Feb. 16, 2000

(87) PCT Pub. No.: WO99/09008

PCT Pub. Date: Feb. 25, 1999

(30) Foreign Application Priority Data

Aug. 18, 1997 (CH) ................................ 1934/97

(51) Int. Cl.[7] ........................ C07D 251/08; A01N 43/40
(52) U.S. Cl. ........................ 514/241; 544/215
(58) Field of Search ................. 544/215, 185; 514/241

(56) References Cited

U.S. PATENT DOCUMENTS 5,245,040 A  *  9/1993  Maienfisch et al. ......... 546/275

FOREIGN PATENT DOCUMENTS

EP         0483 062        * 10/1991

OTHER PUBLICATIONS

Knapp S. et al. J.Org. Chem. 37, 6239–6258, 1992.*

* cited by examiner

Primary Examiner—Mukund J. Shah
Assistant Examiner—Venkataraman Balasubramanian
(74) Attorney, Agent, or Firm—William A. Teoli, Jr.; Rose M. Allen

(57) ABSTRACT

The invention relates to a method for producing an organic compound of formula (I) and optionally its E/Z-isomers, E/Z-isomer mixtures and/or tautomers, each in free or salt form, $R_1$ representing hydrogen or $C_1$–$C_4$ alkyl, $R_2$ representing hydrogen, $C_1$–$C_6$ alkyl, $C_3$–$C_6$ cycloalkyl or a radical —$CH_2B$, Het representing an unsubstituted or substituted heterocyclic radical and B representing phenyl, 3-pyridyl or thiazolyl, these being optionally substituted. The invention is characterized in that a compound of formula (IIa) Q—A—Q, wherein A represents a direct bond or an organic radical, or of formula (IIb), wherein U represents an organic radical, Q representing (1) in the compounds (IIa) and (IIb) and $R_1$, $R_2$ and Het having the meaning given above for formula (I), and optionally their E/Z-isomers, E/Z-isomer mixtures and/or tautomers, each in free or salt form are hydrolyzed. The invention also relates to a method for producing compounds of formulae (IIa), (IIb), (IIIa) and (IIIb), and to a method for combating pests with compounds of formulae (IIa) and (IIb).

2 Claims, No Drawings

METHOD FOR PRODUCING SUBSTITUTED-2-NITROGUANIDINE DERIVATIVES

The present invention relates to a novel type of method of producing substituted 2-nitroguanidine derivatives.

It is known that, in order to produce 1,3-disubstituted 2-nitroguanidines, a further substituent may be introduced into monosubstituted 2-nitroguanidines (e.g. by alkylation) (see e.g. EP patent applications 0.375.907, 0.376.279 and 0.383.091). Owing to the presence of three reactive hydrogen atoms in the monosubstituted 2-nitroguanidines used as the starting material in these reactions, the previously proposed substitution reactions of this kind are often non-selective and lead to undesired substitution products. The mentioned EP patent applications describe the production of 1,3-disubstituted 2-nitroguanidines by reacting monosubstituted nitroisothioureas with primary amines whilst cleaving mercaptan. However, these nitroisothiourea compounds, containing alkylthio leaving groups, which are proposed as starting compounds in the known processes, can only be obtained with difficulty. In addition, in EP-A-0-483.062, a method of producing the compounds of formula (I) by hydrolysis of hexahydro-triazines is described.

It has now been shown that the above-described methods of producing compounds of formula (I) do not satisfy the requirements demanded of a chemical production process, such as availability, toxicity, stability in storage and purity of the starting materials and excipients, reaction time, energy consumption and volumes yielded by the process, quantity and recovery of the accruing by-products and waste products, as well as purity and yield of the end product. There is therefore a need to provide improved methods of producing these compounds. It has now surprisingly been found that the method according to the invention is able to satisfy these requirements to a large extent.

Accordingly, it is the aim of the present invention to provide an improved method of producing 1-monosubstituted and 1,3-disubstituted 2-nitroguanidines from readily obtainable starting compounds, which allows specific 1,3-disubstitution without obtaining major amounts of undesired by-products.

The object of the invention is a) a method of producing a compound of formula

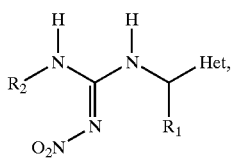
(I)

and, if appropriate, the E/Z isomers, E/Z isomeric mixtures and/or tautomers thereof, each in free form or in salt form, wherein $R_1$ is hydrogen or $C_1$–$C_4$-alkyl;
$R_2$ is hydrogen, $C_1$–$C_6$-alkyl, $C_3$–$C_6$-cycloalkyl or a radical —$CH_2B$;
Het is an aromatic or non-aromatic, monocyclic or bicyclic heterocyclic radical which is unsubstituted or—depending on the substitution possibilities of the ring system—mono- to penta-substituted by substituents selected from the group comprising halogen, $C_1$–$C_3$-alkyl, $C_1$–$C_3$-alkoxy, halogen-$C_1$–$C_3$-alkyl, $C_1$–$C_3$-halogenalkoxy, cyclopropyl, halogencyclopropyl, $C_2$–$C_3$-alkenyl, $C_2$–$C_3$-alkynyl, $C_2$–$C_3$-halogenalkenyl and $C_2$–$C_3$-halogenalkynyl, $C_1$–$C_3$-alkylthio, $C_1$–$C_3$-halogenalkylthio, allyloxy, propargyloxy, allylthio, propargylthio, halogenallyloxy, halogenallylthio, cyano and nitro; and B is phenyl, 3-pyridyl or thiazolyl, which are optionally substituted by one to three substituents from the group comprising $C_1$–$C_3$-alkyl, $C_1$–$C_3$-halogenalkyl, cyclopropyl, halogencyclopropyl, $C_2$–$C_3$-alkenyl, $C_2$–$C_3$-alkynyl, $C_1$–$C_3$-alkoxy, $C_2$–$C_3$-halogenalkenyl, $C_2$–$C_3$-halogenalkynyl, $C_1$–$C_3$-halogenalkoxy, $C_1$–$C_3$-alkylthio, $C_1$–$C_3$-halogenalkylthio, allyloxy, propargyloxy, allylthio, propargylthio, halogenallyloxy, halogenallylthio, halogen, cyano and nitro;

characterised by hydrolysing a compound of formula

(IIa), wherein A is a direct bond or an organic radical; or of formula

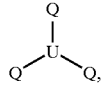
(IIb)

wherein U is an organic radical; and in compounds (IIa) and (IIb) Q signifies

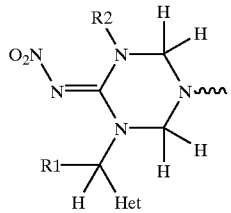

and $R_1$, $R_2$ and Het are as defined above for formula (I), and optionally the E/Z isomers, E/Z isomeric mixtures and/or tautomers thereof, each in free form or in salt form.

The compounds of formula (I) may be present as E/Z isomers, e.g. in the following two isomeric forms

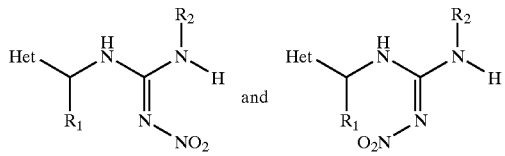

Accordingly, any reference to compounds of formula (I) hereinbefore and hereinafter is understood to include also their corresponding E/Z isomers, even if the latter are not specifically mentioned in each case.

The compounds of formula (I) may be present partly in the form of tautomers. Accordingly, any reference to compounds of formula (I) hereinbefore and hereinafter is understood to include also their corresponding tautomers, even if the latter are not specifically mentioned in each case.

The compounds of formula (I) and, where appropriate, the E/Z isomers and tautomers thereof, may be present as salts. Compounds of formula (I) having at least one basic centre may form e.g. acid addition salts. These are formed for example with strong inorganic acids, such as mineral acids, e.g. sulfuric acid, a phosphoric acid or a hydrohalic acid, or with strong organic carboxylic acids, such as $C_1$–$C_4$alkanecarboxylic acids substituted where appropriate for example by halogen, e.g. acetic acid, such as optionally unsaturated dicarboxylic acids, e.g. oxalic, malonic, maleic, fumaric or phthalic acid, such as hydroxycarboxylic acids, e.g. ascorbic, lactic, malic, tartaric or citric acid, or benzoic acid, or with organic sulfonic acids, typically $C_1$–$C_4$alkane or arylsulfonic acids substituted where appropriate for example by halogen, e.g. methane-, trifluoromethane- or p-toluene-sulfonic acid. Salts of compounds of formula (I) with acids of the said kind are preferably obtained when working up the reaction mixtures.

In a broader sense, compounds of formula (I) with at least one acid group can form salts with bases. Suitable salts with bases are for example metal salts, typically alkali or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl-, diethyl-, triethyl- or dimethylpropylamine, or a mono-, di- or trihydroxy-lower alkylamine, e.g. mono-, di- or triethanolamine. Corresponding internal salts where appropriate may also be formed. Preferred compounds within the scope of this invention are agrochemically advantageous salts. Hereinbefore and hereinafter, the free compounds of formula (I) are understood where appropriate to include also by analogy the corresponding salts, or the salts are understood to include also the free compounds of formula (I). The same applies to E/Z isomers and tautomers of compounds of formula (I) and salts thereof. The free form is preferred.

The statements made about the free compounds of formula (I) or the E/Z isomers and tautomers and salts thereof also apply by analogy to the compounds of formulae (IIa) and (IIb), as well as the compounds of formulae (IIIa) and (IIIb) below.

In the definitions of the above formulae (I), (IIa), (IIb) and of the compounds of formulae (IIIa) and (IIIb) below, the individual generic terms are to be understood as follows:

The halogen atoms considered as substituents may be both fluorine and chlorine, and bromine and iodine, whereby fluorine, chlorine and bromine are preferred, especially chlorine. Halogen in this context is understood to be an independent substituent or part of a substituent, such as in halogenalkyl, halogenalkylthio, halogenalkoxy, halogencycloalkyl, halogenalkenyl, halogenalkynyl, halogenallyloxy or halogenallylthio. The alkyl, alkylthio, alkenyl, alkynyl and alkoxy radicals considered as substituents may be straight-chained or branched. Examples of such alkyls which may be mentioned are methyl, ethyl, propyl, isopropyl, butyl, isobutyl, sec.-butyl or tert.-butyl. Suitable alkoxy radicals which may be mentioned are, inter alia: methoxy, ethoxy, propoxy, isopropoxy or butoxy and the isomers thereof. Alkylthio is for example methylthio, ethylthio, isopropylthio, propylthio or the isomeric butylthio. If the alkyl, alkoxy, alkenyl, alkynyl or cycloalkyl groups considered as substituents are substituted by halogen, they may be only partially halogenated or also perhalogenated. The above-mentioned definitions apply here to halogen, alkyl and alkoxy. Examples of the alkyl elements of these groups are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl, mono- to heptasubstituted by fluorine, chlorine and/or bromine, such as $CH_2CHBrCH_2Br$, $CF_2CHFCF_3$, $CH_2CF_2CF_3$ or $CH(CF_3)_2$; butyl or one of its isomers, mono- to nonasubstituted by fluorine, chlorine and/or bromine, such as $CF(CF_3)CHFCF_3$ or $CH_2(CF_2)_2CF_3$; 2-chlorocyclopropyl or 2,2-difluorocyclopropyl; 2,2-difluorovinyl, 2,2-dichlorovinyl, 2-chloroalkyl, 2,3-dichlorovinyl or 2,3-dibromovinyl.

If the defined alkyl, alkoxy or cycloalkyl groups are substituted by other substituents, they may be mono- or repeatedly substituted by identical or different substituents from those listed. In the substituted groups, it is preferable for one or two further substituents to be present. The cycloalkyl radicals considered as substituents may be, for example, cyclopropyl, cyclobutyl, cyclopentyl or cyclohexyl. Alkenyl and alkynyl groups contain an unsaturated carbon-carbon bond. Typical representatives are allyl, methallyl or propargyl, but also vinyl and ethynyl. The double or triple bonds in allyloxy, propargyloxy, allylthio or propargylthio are separated from the connection point to the hetero atom (O or S) preferably by a saturated carbon atom.

As with the above-mentioned alkyl, alkenyl and alkynyl groups, the alkylene, alkenylene and alkynylene groups defined in the following may also be straight-chained or branched. Examples are —$CH_2$—$CH_2$—, —$CH_2$—$CH_2$—$CH_2$—, —$CH_2$—$CH_2$—$CH_2$—$CH_2$—, —$CH_2$—$C(CH_3)$H— and —$C(CH_3)$H—$C(CH_3)$H—. The alkylene, alkenylene, alkynylene, cycloalkylene, arylene or heterocyclyl groups listed below are, where appropriate, substituted in the same way as the above-mentioned alkyl, alkenyl and alkynyl groups.

Aryl or arylene signifies phenyl or naphthyl, or phenylene or naphthylene, especially phenyl or phenylene.

In the context of the present invention, the heteroaryl radical indicated as Het signifies preferably a 5- to 7-membered, aromatic or non-aromatic ring with one to three hetero atoms selected from the group comprising N, O and S. Preference is given to aromatic 5- and 6-rings, which have a nitrogen atom as the hetero atom and optionally one further hetero atom, preferably nitrogen, oxygen or sulphur, especially nitrogen.

It has now surprisingly been found that the method according to the invention is able to satisfy the requirements mentioned initially.

The hydrolysis process according to the invention may be carried out both in an acidic and in a basic medium. In the acidic range, pH values of 6 or less, especially 1 to 3, are preferred. In the basic range, a pH value greater than 7 and up to 12, especially 8 to 12, in particular 8 to 10, is preferred. The reaction is carried out at normal pressure and at a temperature of 0 to 120° C., preferably 20 to 80° C.

The reaction is carried out in a solvent or diluent that is inert towards the reaction components. Suitable solvents are, in particular, alcohols such as methanol, ethanol, propanol and isopropanol, as well as especially water. Further appropriate solvents are e.g. ethers, such as tetrahydrofuran and dioxane, as well as other solvents which do not adversely affect the reaction. The solvents may also be used as mixtures. A compound of formula (II) is preferably hydrolysed in an aqueous medium or in a mixture of water with an alcohol.

Suitable acids for carrying out the process are preferably mineral acids, e.g. sulfuric acid, a phosphoric acid or a hydrohalic acid, an organic carboxylic acid, typically $C_1$–$C_4$alkanecarboxylic acids substituted where appropriate for example by halogen, e.g. acetic acid, such as dicarboxylic acids that are unsaturated where necessary, e.g. oxalic, malonic, maleic, fumaric or phthalic acid, typically hydroxycarboxylic acids, e.g. ascorbic, lactic, malic, tartaric or citric acid, or benzoic acid, or an organic sulfonic acid, typically $C_1$–$C_4$alkane- or arylsulfonic acids substituted where appropriate for example by halogen, e.g. methanesulfonic or p-toluenesulfonic acid.

Suitable bases for carrying out the process are preferably hydroxides of alkali metals and alkaline earth metals, such as NaOH and KOH, carbonates such as $Na_2CO_3$, $NaHCO_3$, $K_2CO_3$; phosphates such as $Na_3PO_4$, $Na_2HPO_4$, alcoholates such as sodium methaholate, sodium ethanolate and K-tert.-butanolate, organic amines such as morpholine, piperidine, pyrrolidine, a mono-, di- or tri-lower alkylamine, e.g. ethyl-, diethyl, triethyl- or dimethylpropyl-amine, or a mono-, di- or trihydroxy lower alkylamine, e.g. mono-, di- or triethanolamine, or dialkylaniline, for example N,N-dimethyl- or N,N-diethylaniline, as well as salts of organic acids, such as sodium acetate, potassium acetate or sodium benzoate, or mixtures thereof, for example acetate or phosphate buffers.

Especially advantageous reaction conditions are described in the examples.

The method according to the invention is preferably used to produce compounds of formula (I) in which the heterocyclic radical Het is unsaturated and is bonded by a carbon atom as a ring member to the fundamental substance. Especially preferred radicals Het are pyridyl, thiazolyl, tetrahydrofuranyl, dihydrofuranyl, furanyl, N-oxido-pyridinio, oxazolyl, isoxazolyl, thienyl, morpholinyl, piperidinyl, pyridinyl and pyrazinyl; particularly pyridyl, thiazolyl, tetrahydrofuranyl and N-oxido-pyridinio, most particularly 3-pyridyl, 2-halogenpyrid-5-yl, 2,3-dihalogenpyrid-5-yl, 2-halogenthiazol-5-yl, tetrahydrofuran-3-yl, 2-methyl-tetrahydrofuran-4-yl, 1-oxopyrid-3-yl, 1-oxo-2-halogenpyrid-5-yl and 1-oxo-2,3-dihalogenpyrid-5-yl.

Equally preferably, the heterocycles Het carry one to three substituents from the group halogen, $C_1$–$C_3$-alkyl, $C_1$–$C_3$-halogenalkyl and $C_1$–$C_3$-halogenalkoxy each with 1 to 7 halogen atoms, and $C_1$–$C_3$-alkoxy, most preferably chlorine or methyl.

Furthermore, compounds of formula (I) are preferably produced according to the invention, in which the radical B is a phenyl, pyridyl or thiazolyl radical that is unsubstituted or may be substituted by one to two radicals from the group halogen, $C_1$–$C_3$-alkyl, $C_1$–$C_3$-halogenalkyl and $C_1$–$C_3$-halogenalkoxy each with 1 to 7 halogen atoms, and $C_1$–$C_3$-alkoxy.

Of the compounds of formula (I) to be produced according to the invention, the notable ones are those in which $R_1$ is hydrogen;

$R_2$ is hydrogen, $C_1$–$C_3$-alkyl or cyclopropyl; especially hydrogen, methyl, ethyl or cyclopropyl, in particular methyl; and Het is pyridyl, 1-oxopyridyl, tetrahydrofuranyl, thiazolyl; or pyridyl, 1-oxidopyridinio, tetrahydrofuranyl or thiazolyl, respectively substituted by one to three substituents from the group halogen, $C_1$–$C_3$-alkyl, $C_1$–$C_3$-halogenalkyl as well as $C_1$–$C_3$-halogenalkoxy with 1 to 7 halogen atoms and $C_1$–$C_3$-alkoxy;
especially 2-chloropyrid-5-yl, tetrahydrofuran-3-yl, 2-methyl-tetrahydrofuran4-yl or 2-chloro-thiazol-5-yl.

To carry out the process according to the invention, on the one hand preferably those compounds of formula (IIa) are used, in which A is straight-chained or branched $C_2$–$C_{20}$-alkylene, $C_2$–$C_{20}$-alkenylene, $C_2$–$C_{20}$-alkynylene, $C_3$–$C_{12}$-cycloalkylene, arylene or heterocyclylene; whereby the groups $C_2$–$C_{20}$-alkylene, $C_2$–$C_{20}$-alkenylene, $C_2$–$C_{20}$-alkynylene, $C_3$–$C_{12}$-cycloalkylene, arylene and heterocyclylene are optionally substituted once or several times, independently of each other, and the groups $C_2$–$C_{20}$-alkylene, $C_2$–$C_{20}$-alkenylene and $C_2$–$C_{20}$-alkynylene are optionally interrupted once or several times, independently of each other, by O, N—H or N—$C_1$–$C_{12}$-alkyl, $C_3$–$C_9$-cycloalkylene, arylene or heterocyclylene; or a group —$D_1$—$D_2$—$D_3$—; wherein $D_1$ and $D_3$, independently of each other, signify optionally substituted $C_3$–$C_{12}$-cycloalkylene or arylene and $D_2$ signifies $C_2$–$C_{20}$-alkylene, $C_2$–$C_{20}$-alkenylene, $C_2$–$C_{20}$-alkynylene, O, N—H or N—$C_1$–$C_{12}$-alkyl.

Particularly preferred bridging members A are $C_2$–$C_{12}$-alkylene, $C_2$–$C_{12}$-alkylene interrupted by one or two phenylene, cyclohexylene or piperazinylene radicals; cyclohexylene or phenylene; or the group —$D_1$—$D_2$—$D_3$—, wherein $D_1$ and $D_3$ are phenylene or dicyclohexylene and $D_2$ is O or $C_2$–$C_4$-alkylene; A especially signifies $C_2$–$C_4$-alkylene.

On the other hand, in order to carry out the process according to the invention, preferably compounds of formula (IIb) are used as the starting material, wherein U is aryl, heterocyclyl, $C_3$–$C_{12}$-cycloalkyl or a group

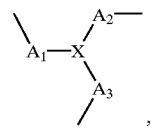

wherein $A_1$, $A_2$ and $A_3$ independently of one another, have the same significances as given above for A in formula (IIa), and X signifies N or CH.

Heterocyclyl A and U in the compounds of formulae (IIa) and (IIb) is preferably an aromatic or non-aromatic, three- to ten-membered ring. If the rings A and U are aromatic, they are preferably the same rings as defined above for Het. If the rings A and U are non-aromatic heterocyclic rings, they are especially piperidinyl, piperazinyl, morpholinyl, pyrrolidinyl, tetrahydrofuranyl and dioxolanyl. The radicals $A_1$, $A_2$ and $A_3$ independently of one another are most preferably $C_2$–$C_4$-alkylene, especially ethylene.

A further object of the invention is b) a method of producing a compound of formula (IIa) and (IIb), in which a compound of formula

           (IIIa), or of formula

           (IIIb)

wherein A and U have the same significance as defined above for formulae (IIa) and (IIb);

T is

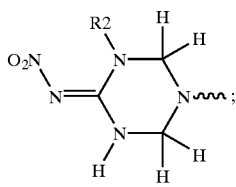

and $R_2$ has the same significance as defined above for formula (I);

and optionally the E/Z isomers, E/Z isomeric mixtures and/or tautomers thereof, each in free form or in salt form, is reacted when producing a compound of formula (IIIa) with two equivalents or when producing a compound of formula (IIIb) with three equivalents of a compound of formula

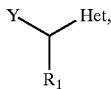

(IV)

which is known or may be produced analogously to methods known per se, wherein $R_1$ and Het are defined as given above for formula (I) and Y is a leaving group, preferably in the presence of a base.

The following may be considered as the leaving group Y in the context of the described method of operation: halogen, preferably chlorine, bromine or iodine, especially chlorine, or sulfonic acid radicals, such as alkylsulfonic acid radicals, mesylate or tosylate.

The process step according to b) may be carried out preferably at normal or at a slightly raised pressure and in the presence of preferably aprotic solvents or diluents. Suitable solvents or diluents are e.g. ethers and ether-type compounds, such as diethyl ether, dipropyl ether, dibutyl ether, dioxane, dimethoxyethane and tetrahydrofuran; aliphatic, aromatic and halogenated hydrocarbons, especially benzene, toluene, xylene, chloroform, methylene chloride, carbon tetrachloride and chlorobenzene; nitriles such as acetonitrile or propionitrile; dimethyl sulfoxide or dimethyl formamide, as well as mixtures of these solvents. This process step is generally carried out at a temperature of −20° C. to +140° C., preferably between 0° C. and +120° C., preferably in the presence of a base. Suitable bases are e.g. carbonates, such as sodium and potassium carbonate. Hydrides may also be used as bases, for example sodium hydride, potassium hydride and calcium hydride. If required, the reaction can also be carried out in the presence of a catalyst, e.g. cesium chloride.

A further object of the invention is c) a method of producing the compounds of formula (IIa) and (IIIb), in which a compound of formula

 (Va), or

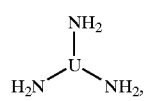 (Vb)

and optionally the E/Z isomers, E/Z isomeric mixtures and/or tautomers thereof, each in free form or in salt form, wherein A and U have the same significance as defined above for the compounds of formulae (IIa) and (IIb), and which are known or may be produced analogously to methods known per se, is reacted when producing a compound of formula (IIIa) either with two equivalents, or when producing a compound of formula (IIIb) with three equivalents of a compound of formula

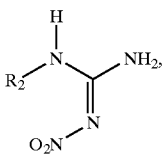

(VI)

which is known or may be produced analogously to methods known per se, and wherein $R_2$ has the same significance as defined for formula (I), in the presence of an excess of formaldehyde or paraformaldehyde.

The process according to c) for the preparation of the compounds of formula (III) is advantageously carried out at normal pressure, but also optionally at a raised pressure in the presence of an inert solvent and at temperatures of between 0C and +140° C., preferably between +20° C. and +120° C. Suitable solvents are, in particular, alcohols such as methanol, ethanol, and propanol, as well as water. Further suitable solvents are e.g. aromatic hydrocarbons, such as benzene, toluene and xylene; ethers such as tetrahydrofuran, dioxane and diethyl ether, halogenated hydrocarbons such as methylene chloride, chloroform, carbon tetrachloride and chlorobenzene, as well as other solvents which to not impair the reaction. The solvents may also be used as mixtures. The process is optionally effected adding an acidic catalyst, such as HCl, $H_2SO_4$ or a sulfonic acid, such as p-toluene-sulfonic acid. The resulting reaction water may be removed, if desired, using a water separator or by adding a molecular sieve.

A further object of the invention is d) a method of producing a compound of formula (I), in which a compound of formula (Va) or (Vb) is converted into a compound of formula (IIIa) or (IIIb) by reacting it with a compound of formula (VI) and formaldehyde or paraformaldehyde; this compound of formula (IIIa) or (IIIb) is converted by a compound of formula (IV) into a compound of formula (IIa) or (IIb) and this compound of formula (IIa) or (IIb) is hydrolysed.

Further objects of the invention are the compounds of formulae (IIa), (IIb), (IIIa) and (IIIb), and optionally the E/Z isomers, E/Z isomeric mixtures and/or tautomers thereof, each in free form or in salt form, as well as the use thereof in the preparation of compounds of formula (I).

Especially preferred embodiments of the method according to variants b) to d) may be taken from the examples.

The compounds of formula (I) produced according to the invention are known. They are valuable active ingredients in pest control, that are well tolerated by warm-blooded animals, fish and plants. The compounds of formula (I) are especially suitable for the control of insects and arachnids, which appear on crops and ornamentals in agriculture, especially in cotton, vegetable and fruit plantations, in forestry, in the protection of stock and material, as well as in the hygiene sector, especially on domestic animals and productive livestock. The compounds are especially effective against plant-damaging sucking insects, especially against aphids and plant and leaf hoppers.

EXAMPLE P1.1

Preparation of the compound of formula

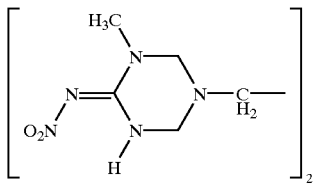

A mixture of 3.0 g of 1-methyl-2-nitroguanidine, 0.85 g of 1,2-diaminoethane, 15 ml of dioxane and 5.7 ml of a 37% solution of formaldehyde in water at room temperature is heated to 50° C. and stirred at this temperature for 4 hours. The mixture is then evaporated to dryness under vacuum, the residue stirred with diethyl ether and the title compound isolated by filtration. M.p. 222–223° C. (compound 1.1).

EXAMPLE P1.2

Preparation of the compound of formula

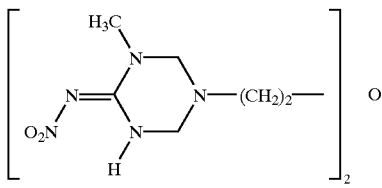

A mixture of 1.8 g of 1-methyl-2-nitroguanidine, 1.35 9 of paraformaldehyde and 0.78 g of 1,5-diamino-3-oxa-pentane in 20 ml of toluene and 20 ml of dioxane is mixed at room temperature with two drops of a 37% solution of HCl in water, then heated to reflux temperature and stirred at this temperature for 6 hours. The mixture is then evaporated to dryness under vacuum, the residue stirred with diethyl ether and the title compound isolated by filtration (compound 1.15).

EXAMPLE P1.3

Preparation of the compound of formula

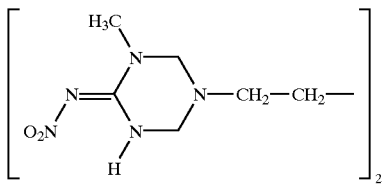

A mixture of 8.0 g of 1-methyl-2-nitroguanidine and 3.0 g of 1,4-diaminobutane in 25 ml of ethanol is mixed at room temperature with 25 ml of a 37% solution of formaldehyde in water, heated to 50° C. and stirred at this temperature for 16 hours. Then, the mixture is evaporated to dryness under vacuum, and the residue is stirred with ethanol. The title compound is obtained with a melting point of 232–234° C. (compound 1.4).

EXAMPLE P1.4

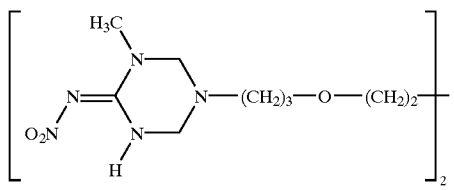

A mixture of 6.0 g of 1-methyl-2-nitroguanidine and 5.4 g of 4,9dioxa-1,12-diaminododecane in 25 ml of ethanol is mixed at room temperature with 19 ml of a 37% solution of formaldehyde in water, heated to 50° C. and stirred at this temperature for 16 hours. Then, the mixture is cooled to 5° C., filtered and the residue washed with a little ethanol. The title compound is obtained with a melting point of 140–143° C. (compound 1.14).

EXAMPLE P1.5

The following compounds listed in Table 1 can also be obtained analogously to the above methods of examples P1.1 to P1.4.

TABLE 1

Compounds of formula

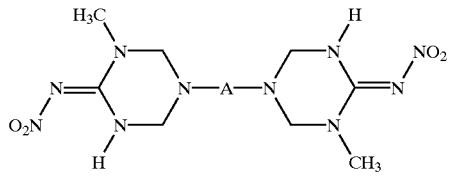

| No. | A | phys. data |
|---|---|---|
| 1.1 | —(CH$_2$)$_2$— | m.p. 222–223° C. |
| 1.2 | —CH(CH$_3$)—CH$_2$— | |
| 1.3 | —(CH$_2$)$_3$— | |
| 1.4 | —(CH$_2$)$_4$— | m.p. 232–234° C. |
| 1.5 | —(CH$_2$)$_5$— | |
| 1.6 | —(CH$_2$)$_6$— | |
| 1.7 | —(CH$_2$)$_7$— | |
| 1.8 | —(CH$_2$)$_8$— | |
| 1.9 | —(CH$_2$)$_9$— | |
| 1.10 | —(CH$_2$)$_{10}$— | |
| 1.11 | —(CH$_2$)$_{12}$— | |
| 1.12 | —CH$_2$—C(CH$_3$)$_2$—CH$_2$— | |
| 1.13 | —CH$_2$—CH(OH)—CH$_2$— | |
| 1.14 | —(CH$_2$)$_3$—O—(CH$_2$)$_4$—O—(CH$_2$)$_3$— | m.p. 140–143° C. |
| 1.15 | —CH$_2$—CH$_2$—O—CH$_2$—CH$_2$— | |
| 1.16 | —CH$_2$—CH(CH$_3$)—(CH$_2$)$_3$— | |
| 1.17 | —(CH$_2$)$_2$—O—(CH$_2$)$_2$—O—(CH$_2$)$_2$— | |
| 1.18 | —(CH$_2$)$_3$—O—(CH$_2$)$_2$—O—(CH$_2$)$_2$—O—(CH$_2$)$_3$— | |
| 1.19 | —(CH$_2$)$_3$—N(CH$_3$)—(CH$_2$)$_3$— | |
| 1.20 | | |

TABLE 1-continued

Compounds of formula

| No. | A | phys. data |
|---|---|---|
| 1.21 | 1,3-diethylcyclohexyl group | |
| 1.22 | bis(4-methylcyclohexyl)methane group | |
| 1.23 | —(CH₂)₃—N(piperazine)N—(CH₂)₃— | |
| 1.24 | 1,3-dimethylphenyl | |
| 1.25 | 1,4-dimethylphenyl | |
| 1.26 | bis(4-methylphenyl)ether | |
| 1.27 | bis(4-methylphenyl)methane | |
| 1.28 | 1,3-bis(4-methylphenyl)propane | |
| 1.29 | 1,4-diethylbenzene | |
| 1.30 | bis(3-methylphenyl)methane | |

EXAMPLE P2.1

Preparation of the compound of formula

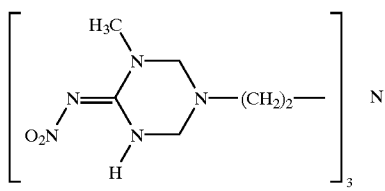

A mixture of 2.4 g of 1-methyl-2-nitroguanidine and 1.0 g of tris(2-aminoethyl)amine in 50 ml of ethanol is mixed at room temperature with 30 ml of a 37% solution of formaldehyde in water, heated to 50° C. and stirred at this temperature for 16 hours. The mixture is then evaporated to dryness under vacuum, the residue stirred with diethyl ether/ethyl acetate (1:1) and the title compound isolated by filtration (compound 2.1).

EXAMPLE P2.2

The following compounds listed in Table 2 can also be obtained analogously to the above method of example P2.1.

TABLE 2

Compounds of formula

| No. | A₁ | A₂ | A₃ | X | phys. data |
|---|---|---|---|---|---|
| 2.1. | —(CH₂)₂— | —(CH₂)₂— | —(CH₂)₂— | N | |
| 2.2. | —(CH₂)₃ | —CH₂— | —(CH₂)₄ | CH | |

EXAMPLE P3.1

Preparation of the compound of formula

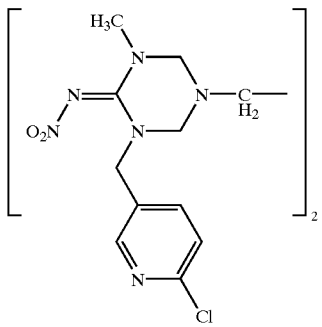

A mixture of 2.0 g of the product obtainable according to example P1.1, 1.6 g of 2-chloro-5-chloromethylpyridine and 2.8 g of potassium carbonate in 20 ml of dimethylformamide is stirred for 9 hours at 90° C. Then, the reaction mixture is filtered, the filtrate concentrated by evaporation under vacuum, and the residue taken up in 100 ml of dichloromethane. The organic phase is washed with 50 ml of water and 50 ml of saturated sodium chloride solution, dried over $MgSO_4$ and evaporated to dryness. The residue is stirred with diethyl ether and the title compound isolated by filtration (compound 10.B.1).

EXAMPLE P3.2

Preparation of the compound of formula

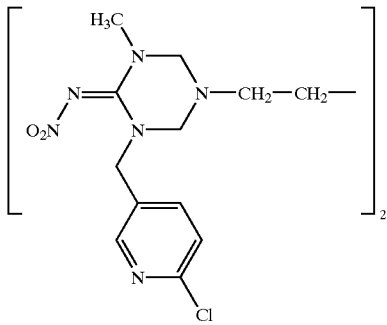

A mixture of 3.7 g of the compound obtainable according to example P1.3, 3.2 g of 2-chloro-5-chloromethylpyridine and 5.5 g of potassium carbonate in 20 ml of dimethylformamide is stirred for 16 hours at 55° C. Then, the reaction mixture is filtered, the filtrate is concentrated by evaporation under vacuum, the residue is stirred in methanol and filtration carried out. This yields the title compound with a melting point of 178–180° C. (compound 10.B.4).

EXAMPLE P3.3

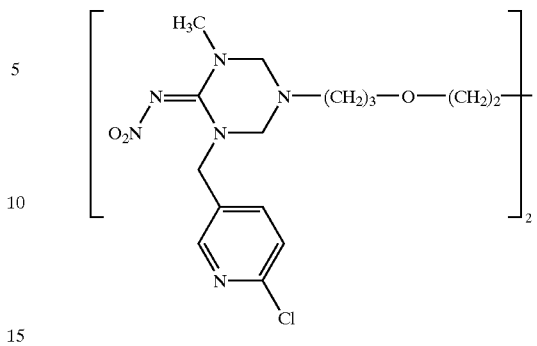

A mixture of 4.9 g of the compound obtainable according to example P1.4, 3.24 g of 2-chloro-5-chloromethylpyridine and 5.5 g of potassium carbonate in 20 ml of dimethylformamide is stirred for 16 hours at 55° C. Then, the reaction mixture is filtered, the filtrate concentrated by evaporation under vacuum, and the residue purified on silica gel with ethyl acetate/methanol (2:1) as eluant. This yields the title compound with a melting point of 70–72° C. (compound 10.B.14).

EXAMPLE P3.4

Compound of formula

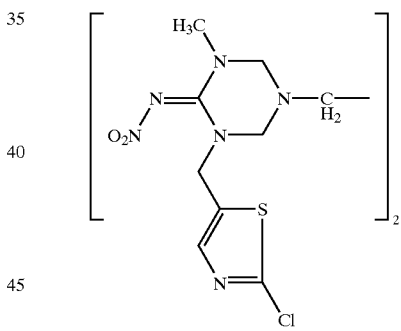

A mixture of 2.0 9 of the compound obtainable according to example P1.1, 1.95 g of 2-chloro-5-chloromethylthiazole, 4.0 g of potassium carbonate and 1.53 g of 18-Crown-6 (1,5,7,10,13,16-hexaoxacyclooctadecane) in 20 ml of tetrahydrofuran is stirred for 24 hours at 50° C. Then, the reaction mixture is filtered, the filtrate concentrated by evaporation under vacuum, and the residue purified on silica gel with dichloromethane/methanol (9:1) as eluant. This yields the title compound with a melting point of 175–178° C. (compound 3.B.1).

EXAMPLE P3.5

The following compounds listed in Tables 3 to 26 can also be obtained analogously to the above methods of examples P3.1 to P3.4.

TABLE B

Compounds of formula

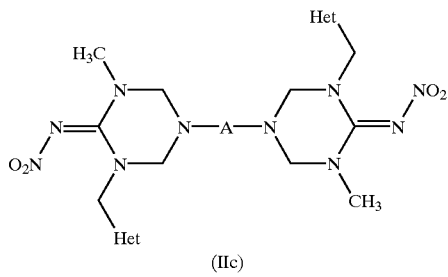

(IIc)

| No. | A |
|---|---|
| B.1 | —(CH$_2$)$_2$— |
| B.2 | —CH(CH$_3$)—CH$_2$— |
| B.3 | —(CH$_2$)$_3$— |
| B.4 | —(CH$_2$)$_4$— |
| B.5 | —(CH$_2$)$_5$— |
| B.6 | —(CH$_2$)$_6$— |
| B.7 | —(CH$_2$)$_7$— |
| B.8 | —(CH$_2$)$_8$— |
| B.9 | —(CH$_2$)$_9$— |
| B.10 | —(CH$_2$)$_{10}$— |
| B.11 | —(CH$_2$)$_{12}$— |
| B.12 | —CH$_2$—C(CH$_3$)$_2$—CH$_2$— |
| B.13 | —CH$_2$—CH(OH)—CH$_2$— |
| B.14 | —(CH$_2$)$_3$—O—(CH$_2$)$_4$—O—(CH$_2$)$_3$— |
| B.15 | —CH$_2$—CH$_2$—O—CH$_2$—CH$_2$— |
| B.16 | —CH$_2$—CH(CH$_3$)—(CH$_2$)$_3$— |
| B.17 | —(CH$_2$)$_2$—O—(CH$_2$)$_2$—O—(CH$_2$)$_2$— |
| B.18 | —(CH$_2$)$_3$—O—(CH$_2$)$_2$—O—(CH$_2$)$_2$—O—(CH$_2$)$_3$— |
| B.19 | —(CH$_2$)$_3$—N(CH$_3$)—(CH$_2$)$_3$— |
| B.20 | ![cyclohexane-1,3-diyl] |
| B.21 | ![cyclohexane bis(ethyl)] |
| B.22 | ![bis(methylcyclohexyl)methane] |
| B.23 | —(CH$_2$)$_3$—N(piperazine)N—(CH$_2$)$_3$— |
| B.24 | ![m-phenylene bis(methyl)] |
| B.25 | ![p-phenylene bis(methyl)] |
| B.26 | ![bis(4-methylphenyl) ether] |

TABLE B-continued

Compounds of formula

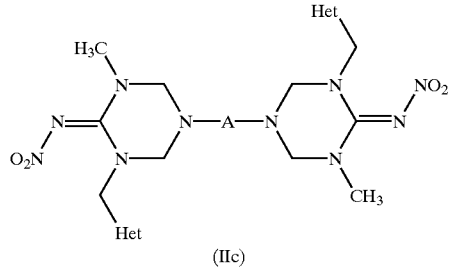

(IIc)

| No. | A |
|---|---|
| B.27 | ![4,4'-bis(methyl)diphenylmethane] |
| B.28 | ![4,4'-bis(methyl)diphenylpropane] |
| B.29 | ![p-phenylene bis(ethyl)] |
| B.30 | ![3,3'-bis(methyl)diphenylmethane] |

Table 3: Compounds of the general formula (IIc), wherein Het signifies

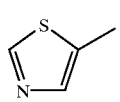

and A corresponds in each case to one line of Table B.
Compound 3.B.01: m.p. 175–178° C.

Table 4: Compounds of the general formula (IIc), wherein Het signifies

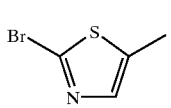

and A corresponds in each case to one line of Table B.

Table 5: Compounds of the general formula (IIc), wherein Het signifies and A corresponds in each case to one line of Table B.

Table 6: Compounds of the general formula (IIc), wherein Het signifies

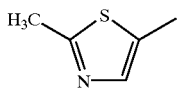

and A corresponds in each case to one line of Table B.

Table 7: Compounds of the general formula (IIc), wherein Het signifies 2-methyl-tetrafuran-4-yl and A corresponds in each case to one line of Table B.

Table 8: Compounds of the general formula (IIc), wherein Het signifies tetrafuran-3-yl and A corresponds in each case to one line of Table B.

Table 9: Compounds of the general formula (IIc), wherein Het signifies

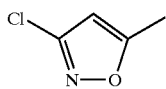

and A corresponds in each case to one line of Table B.

Table 10: Compounds of the general formula (IIc), wherein Het signifies

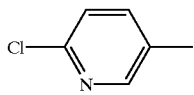

and A corresponds in each case to one line of Table B.

Compound 10.B.04: m.p. 178–180° C.

Compound 10.B.14: m.p. 70–72° C.

Table 11: Compounds of the general formula (IIc), wherein Het signifies pyrid-3-yl and A corresponds in each case to one line of Table B.

Table 12: Compounds of the general formula (IIc), wherein Het signifies

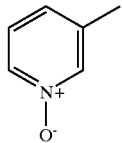

and A corresponds in each case to one line of Table B.

Table 13: Compounds of the general formula (IIc), wherein Het signifies

and A corresponds in each case to one line of Table B.

Table 14: Compounds of the general formula (IIc), wherein Het signifies 2,3-dichloropyrid-5-yl and A corresponds in each case to one line of Table B.

TABLE C

Compounds of formula

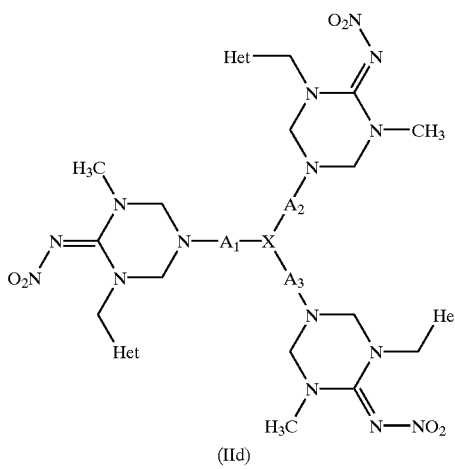

(IId)

| No. | $A_1$ | $A_2$ | $A_3$ | X |
|---|---|---|---|---|
| C.1 | $-(CH_2)_2-$ | $-(CH_2)_2-$ | $-(CH_2)_2-$ | N |
| C.2 | $-(CH_2)_3-$ | $-CH_2-$ | $-(CH_2)_4-$ | CH |

Table 15: Compounds of the general formula (IId), wherein Het signifies

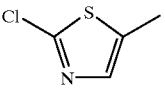

and $A_1$, $A_2$, $A_3$ and X correspond in each case to one line of Table C.

Table 16: Compounds of the general formula (IId), wherein Het signifies

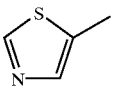

and $A_1$, $A_2$, $A_3$ and X correspond in each case to one line of Table C.

Table 17: Compounds of the general formula (IId), wherein Het signifies

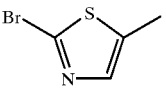

and $A_1$, $A_2$, $A_3$ and X correspond in each case to one line of Table C.

Table 18: Compounds of the general formula (IId), wherein Het signifies

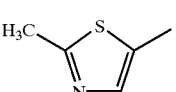

and $A_1$, $A_2$, $A_3$ and X correspond in each case to one line of Table C.

Table 19: Compounds of the general formula (IId), wherein Het signifies 2-methyl-tetrahydrofuran-4-yl and $A_1$, $A_2$, $A_3$ and X correspond in each case to one line of Table C.

Table 20: Compounds of the general formula (IId), wherein Het signifies 3-tetrahydrofuranyl and $A_1$, $A_2$, $A_3$ and X correspond in each case to one line of Table C.

Table 21: Compounds of the general formula (IId), wherein Het signifies

[structure: 3-chloro-5-methyl-isoxazole]

and $A_1$, $A_2$, $A_3$ and X correspond in each case to one line of Table C.

Table 22: Compounds of the general formula (IId), wherein Het signifies 2-chloro-pyrid-5-yl and $A_1$, $A_2$, $A_3$ and X correspond in each case to one line of Table C.

Table 23: Compounds of the general formula (IId), wherein Het signifies 3-pyridyl and $A_1$, $A_2$, $A_3$ and X correspond in each case to one line of Table C.

Table 24: Compounds of the general formula (IId), wherein Het signifies

[structure: 3-methylpyridine N-oxide]

and $A_1$, $A_2$, $A_3$ and X correspond in each case to one line of Table C.

Table 25: Compounds of the general formula (IId), wherein Het signifies

[structure: 2-chloro-5-methylpyridine N-oxide]

$A_1$, $A_2$, $A_3$ and X correspond in each case to one line of Table C.

Table 26: Compounds of the general formula (IId), wherein Het signifies 2,3-dichloropyrid-5-yl and $A_1$, $A_2$, $A_3$ and X correspond in each case to one line of Table C.

EXAMPLE 4.1

Preparation of the compound of formula

[structure with $H_3C$, NH, NH, $NO_2$ and 2-chloropyrid-5-yl methyl]

1.2 g of the compound obtainable according to example P3.1 are stirred for 16 hours at room temperature together with 10 ml of methanol and 10 ml of 1 n hydrochloric acid. The reaction mixture is concentrated to dryness by evaporation and the residue purified on silica gel with dichloromethane/methanol (95:5) as the eluant. This yields the title product with a melting point of 147–149° C. (compound 27.6).

EXAMPLE 4.2

Preparation of the compound of formula

[structure with $H_3C$, NH, NH, $NO_2$ and 2-chlorothiazol-5-yl methyl]

1.2 g of the compound obtainable according to example P3.4 are stirred for 40 hours at 50° C. together with 3.3 ml of methanol and 3.3 ml of 1 n hydrochloric acid. The reaction mixture is evaporated to dryness and the residue recrystallised from methanol. This yields the title product with a melting point of 170–172° C. (compound 27.1).

EXAMPLE P4.3

The following compounds listed in Table 27 can also be obtained analogously to the above methods of examples 4.1 and 4.2.

TABLE 27

Compounds of the general formula

[structure (I): $H_3C$–NH–C(=N–$NO_2$)–N(H)–CH$_2$–Het]

| No. | Het | Phys. data |
|---|---|---|
| 27.1 | [2-chloro-thiazol-5-yl] | m.p. 170–172° C. |
| 27.2 | [2-methyl-thiazol-5-yl] | |
| 27.3 | pyridyl | |
| 27.4 | [2-bromo-thiazol-5-yl] | m.p. 166–168° C. |
| 27.5 | [tetrahydrofuran-3-yl] | |
| 27.6 | 2-chloropyrid-5-yl | 147–149° C. |
| 27.7 | [2-chloro-5-methylpyridine N-oxide] | |

TABLE 27-continued

Compounds of the general formula

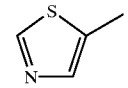

(I)

| No. | Het | Phys. data |
|---|---|---|
| 27.8 | 2,3-dichloropyrid-5-yl | m.p. 173–174° C. |
| 27.9 | 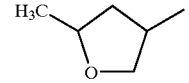 | |
| 27.10 | 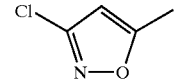 | |
| 27.11 | 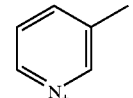 | |
| 27.12 | 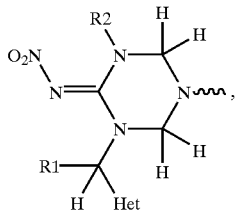 | |

A further object of the invention is a method of controlling pests, especially animal pests, particularly insects and members of the order Acarina, using the compounds of formulae (IIa) and (IIb). The said animal pests include, for example, those which are mentioned in the European Patent application EP-A-736'252. The pests mentioned therein are thus included by reference in the object of the present invention. The method of controlling the said pests and the composition and preparation of the corresponding pesticides are described in EP-A-736'252 and are included by reference in the object of the present invention.

What is claimed is:

1. A compound of formula $$Q-A-Q \qquad (IIa),$$

wherein

A is a direct bond, $C_2$–$C_{12}$-alkylene, $C_2$–$C_{12}$-alkylene interrupted by one or two phenylene, cyclohexylene or piperazinylene radicals; cyclohexylene or phenylene; or the group —$D_1$—$D_2$—$D_3$—, wherein $D_1$ and $D_3$ are phenylene or dicyclohexylene and $D_2$ is 0 or $C_2$–$C_4$-alkylene;

Q is

wherein $R_1$ is hydrogen or $C_1$–$C_4$-alkyl;

$R_2$ is hydrogen, $C_1$–$C_6$-alkyl, $C_3$–$C_6$-cycloalkyl; and

Het is 2-chloropyrid-5-yl, tetrahydrofuran-3-yl, 5-methyl-tetrahydrofuran-3-yl or 2-chloro-thiazol-5-yl;

and optionally the E/Z isomer, E/Z isomeric mixtures and/or tautomers thereof, each in free base form or in salt form.

2. A method of controlling insects and members of the order Acarina, wherein a pesticidally effective amount of the compound of formula (IIa) as defined in claim 1, is applied to the pests or the locus thereof.

* * * * *